US00PP13343P2

(12) United States Plant Patent
Sorensen

(10) Patent No.: US PP13,343 P2
(45) Date of Patent: Dec. 10, 2002

(54) OSTEOSPERMUM PLANT NAMED 'MALINDI'

(75) Inventor: Carl Aksel Kragh Sorensen, Aabyhøj (DK)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/968,314

(22) Filed: Sep. 30, 2001

(51) Int. Cl.[7] ..... A01H 5/00

(52) U.S. Cl. ..... Plt./360
(58) Field of Search ..... Plt./360

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Osteospermum plant named 'Malindi', characterized by its uniformly mounded and outwardly spreading plant habit; freely branching growth habit; full and dense plants; freely flowering habit; dark green foliage; and purple-colored ray florets and dark purple-colored disc florets.

1 Drawing Sheet

BACKGROUND OF THE INVENTION

The present Invention relates to a new and distinct cultivar of Osteospermum plant, botanically known as *Osteospermum ecklonis*, and hereinafter referred to by the name 'Malindi'.

The new Osteospermum is a product of a planned breeding program conducted by the Inventor in Aabyhøj, Denmark. The objective of the breeding program is to create new Osteospermum cultivars with uniform plant habit and interesting floret colors.

The new Osteospermum originated from a cross made by the Inventor during the summer of 1997 of the *Osteospermum ecklonis* cultivar Mansa, not patented, as the female, or seed, parent with an unidentified *Osteospermum ecklonis* selection, not patented, as the male, or pollen, parent. The new Osetospermum was discovered and selected by the Inventor as a single flowering plant within the progeny of the stated cross grown in a controlled environment in Aabyhøj, Denmark.

Asexual reproduction of the new Osteospermum by vegetative tip cuttings was first conducted in Aabyhøj, Denmark in February, 1998. Asexual reproduction by cuttings has shown that the unique features of this new Osteospermum are stable and reproduced true to type in successive generations.

SUMMARY OF THE INVENTION

The cultivar Malindi has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Malindi'. These characteristics in combination distinguish 'Malindi' as a new and distinct Osteospermum:

1. Uniformly mounded and outwardly spreading plant habit.

2. Freely branching growth habit; full and dense plants.

3. Freely flowering habit.

4. Dark green foliage.

5. Purple-colored ray florets and dark purple-colored disc florets.

The new Osteospermum can be compared to plants of the female parent, the cultivar Mansa. In side-by-side comparisons conducted in Encinitas, Calif., plants of the new Osteospermum differed from plants of the cultivar Mansa in the following characteristics:

1. Plants of the new Osteospermum were larger and not as compact than plants of the cultivar Mansa.

2. Inflorescences of plants of the new Osteospermum were fragrant whereas inflorescences of plants of the cultivar Mansa were not fragrant.

3. Ray florets of plants of the new Osteospermum were lighter in color than ray florets of plants of the cultivar Mansa.

Plants of the new Osteospermum differ primarily from plants of the male parent, the unidentified Osteospermum selection, in ray floret coloration.

The new Osteospermum can also be compared to plants of the cultivar Bamba, disclosed in U.S. Plant patent application Ser. No. 09/291,101. In side-by-side comparisons conducted in Encinitas, Calif., plants of the new Osteospermum differed from plants of the cultivar Bamba in the following characteristics:

1. Inflorescence of plants of the new Osteospermum had more ray florets than inflorescences of plants of the cultivar Bamba.

2. Inflorescences of plants of the new Osterspermum were fragrant whereas inflorescences of plants of the cultivar Bamba were not fragrant.

3. Ray florets of plants of the new Osterspermum were lighter in color than ray florets of plants of the cultivar Bamba.

BRIEF DESCRIPTION OF THE PHOTOGRAPHS

The accompanying colored photographs illustrate the overall appearance of the new Osterspermum showing the colors as true as it is reasonably possible to obtain in colored reproductions of this type. Colors in the photographs may differ from the color values cited in the detailed botanical description which accurately describe the colors of the new Osteospermum.

The photograph at the top of the sheet comprises a side perspective view of three typical flowering plants of 'Malindi' grown in a 22-cm container.

The photograph at the bottom of the sheet is a close-up view of typical leaves, inflorescences and inflorescence buds of 'Malindi'.

DETAILED BOTANICAL DESCRIPTION

In the following description, color references are made to The Royal Horticultural Society Colour Chart except where general terms of ordinary dictionary significance are used. The aforementioned photographs, following observations and averaged measurements describe plants grown during the late winter and early spring in Encinitas, Calif., in polyethylene-covered greenhouses and under conditions which approximate those generally used in commercial Osteospermum production. Three rooted cuttings were planted in 22-cm containers and pinched once. During the production of the plants, day temperatures were about 24° C., night temperatures were about 19° C., and light levels were about 4,000 foot-candles. Measurements and numerical values represent averages of typical flowering plants about 18 weeks after planting.

Botanical classification: *Osteospermum ecklonis* cultivar Malindi.

Parentage:

*Female, or seed, parent.*—*Osteospermum ecklonis* cultivar Mansa, not patented.

*Male, or pollen, parent.*—Unidentified *Osteospermum ecklonis* selection, not patented.

Propagation:

*Type.*—Terminal cuttings.

*Time to initiate rooting.*—About 10 days at 18° C.

*Time to develop roots.*—About 24 days at 18° C.

*Root description.*—Fibrous and well-branched.

Plant description:

*Appearance.*—Perennial herbaceous container and garden plant. Uniformly mounded plant habit; upright to outwardly spreading. Freely branching, about seven lateral branches develop after pinching; dense and full plants. Moderately vigorous growth habit.

*Plant height.*—About 40 cm.

*Plant width or area of spread.*—All three plants, about 54 cm; individual plants, about 29 cm.

*Lateral branches.*—Length: About 32 cm. Diameter: About 6 mm. Internode length: About 1.3 cm. Aspect: Upright to outward. Strength: Strong, but tallest lateral branches may tend to bend with the weight of the inflorescences. Texture: Glabrous. Color: 144C.

*Foliage description.*—Arrangement: Alternate; simple. Numbers of leaves per lateral branch: About 20. Length: About 5.5 cm. Width: About 2 cm. Shape: Elliptic. Apex: Broadly acute. Base: Attenuate. Margin: Nearly entire with occasional tiny serrations. Venation pattern: Pinnate. Texture: Coarse, leathery, glandular and glabrous. Color: Young foliage, upper surface: 143A. Young foliage, lower surface: 143B. Fully expanded foliage, upper surface: 147A. Fully expanded foliage, lower surface: 147B. Venation, upper surface: 147D. Venation, lower surface: 147C. Petiole: Length: About 1.5 cm. Diameter: About 5 mm. Texture, upper and lower surfaces: Glabrous. Color: Upper surface: 144B. Lower surface: 144A.

Inflorescence description:

*Appearance.*—Terminal and axillary inflorescences held above and beyond the foliage on moderately strong peduncles. Composite inflorescence form, radially symmetrical, with ligulate-shaped ray florets and disc florets massed at the center; ray and disc florets arranged acropetally on a capitulum. Inflorescences persistent. Inflorescences face upright or outward.

*Flowering response.*—Plants flower continuous and freely from the spring through the fall.

*Postproduction longevity.*—Inflorescences maintain good color and substance for about one week on the plant when grown in an outdoor environment.

*Quantity of inflorescences.*—Freely flowering; at one time, about 80 open inflorescences and buds per plant.

*Fragrance.*—Slightly fragrant; spicy.

*Inflorescence bud (at stage of showing color).*—Length: About 1.8 cm. Diameter: About 8 mm. Shape: Ovoid. Color, ray florets, lower or outer surface: 86C.

*Inflorescence size.*—Diameter: About 6 cm. Depth (height): About 2.2 cm. Disc diameter: About 1.2 cm. Receptacle diameter: About 2 cm. Receptacle height: About 1.2 cm.

*Ray florets.*—Length: About 3 cm. Width: About 8 mm. Shape: Ligulate. Apex: Rounded to slightly emarginate. Base: Acute. Margin: Entire. Texture: Satiny to velvety. Orientation: Initially upright then about 60° from vertical. Number of ray florets per inflorescence: About 20 in a single whorl. Color: When opening, upper surface: 81A. When opening, lower surface: Ground color, 86B with longitudinal stripes, 86A. Fully opened, upper surface: 87A; color does not fade with subsequent development. Fully opened, lower surface: Ground color, 87D with longitudinal stripes, 79A.

*Disc florets.*—Shape: Tubular, elongated. Apex: Five-pointed. Length: About 9 mm. Width: At apex: About 2 mm. At base: About 1 mm. Number of disc florets per inflorescence: About 70. Color: Immature: 90A to 90B. Mature: Apex and mid-section: 90B. Base: 90D.

*Phyllaries.*—Length: About 1.4 cm. Diameter: About 2 mm. Shape: Linear. Apex: Acute. Base: Fused. Margin: Entire. Texture: Slightly coarse with tiny hairs. Number of inflorescence: About 16 in a single whorl. Color: Upper surface: 144B. Lower surface: 144A.

*Peduncles.*—Length, terminal peduncle: About 12 cm. Length, second peduncle: About 8.5 cm. Length, third peduncle: About 10 cm. Diameter: About 2 mm. Angle: Terminal peduncles, erect; secondary and tertiary peduncles, about 45° from vertical. Strength: Moderate, tend to bend with weight of inflorescences. Texture: Coarse with tiny scattered short hairs. Color: 144A.

*Reproductive organs.*—Androecium: Present on disc florets only. Stamen number: Five per floret; fused around style. Anther shape: Oblong. Anther size: About 2 mm by 1 mm. Anther color: 79B. Pollen amount: Scarce to moderate. Pollen color: 23B. Gynoecium: Present on both ray and disc florets. Pistil number: One per floret. Pistil length: About 1 cm. Stigma shape: Two-parted. Stigma color: 79A. Style length: About 5 mm. Style color: 79C. Ovary color: 144D.

*Seed.*—Seed production has not been observed.

Disease/pest resistance: Resistance to pathogens and pests common to Osteospermums has not been observed on plants grown under commercial greenhouse or outdoor conditions.

Temperature tolerance: Plants of the new Osteospermum have been observed to tolerate temperatures from 4° to 32° C.

It is claimed:

1. A new and distinct cultivar of Osteospermum plant named 'Malindi', as illustrated and described.

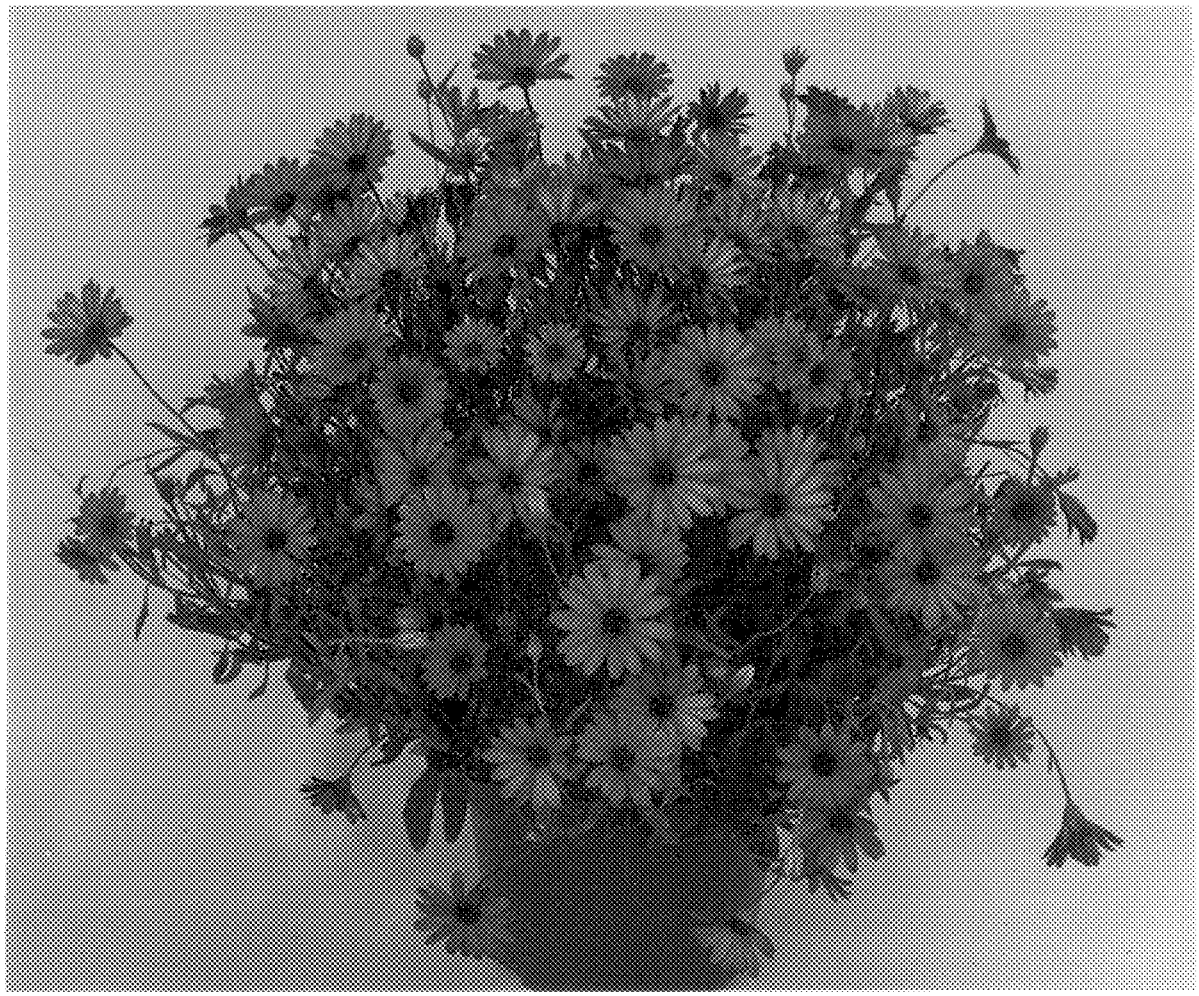
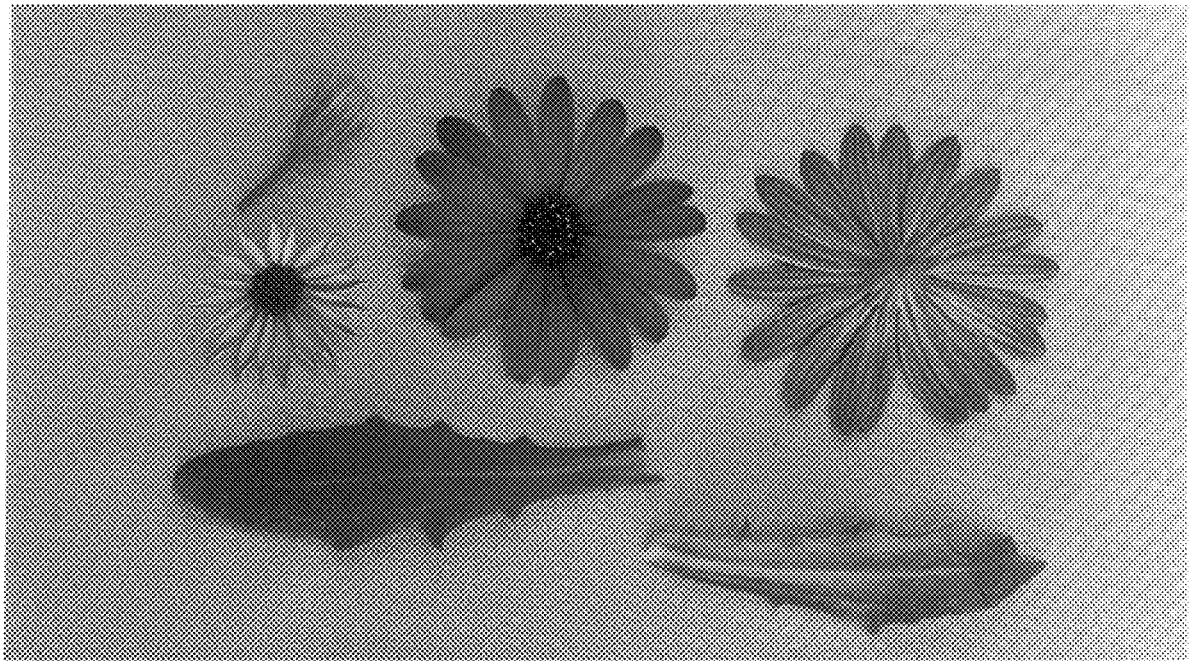

* * * * *